US012780762B2

(12) United States Patent
Russell

(10) Patent No.: US 12,780,762 B2
(45) Date of Patent: Nov. 3, 2026

(54) INTEGRATED STEAM CRACKING AND HYDROGEN PRODUCTION PROCESS

(71) Applicant: UOP LLC, Des Plaines, IL (US)

(72) Inventor: Bradley Russell, Fall Branch, TN (US)

(73) Assignee: UOP LLC, Des Plaines, IL (US)

( * ) Notice: Subject to any disclaimer, the term of this patent is extended or adjusted under 35 U.S.C. 154(b) by 189 days.

(21) Appl. No.: 18/517,268

(22) Filed: Nov. 22, 2023

(65) Prior Publication Data

US 2025/0162964 A1 May 22, 2025

(51) Int. Cl.
*C07C 4/04* (2006.01)
*B01D 53/00* (2006.01)
(Continued)

(52) U.S. Cl.
CPC .............. *C07C 4/04* (2013.01); *B01D 53/002* (2013.01); *B01D 53/047* (2013.01); *B01D 53/226* (2013.01); *B01D 53/229* (2013.01); *B01D 53/265* (2013.01); *C01B 3/24* (2013.01); *C01B 3/36* (2013.01); *C01B 3/48* (2013.01); *C01B 3/501* (2013.01); *C01B 3/506* (2013.01); *C01B 3/56* (2013.01); *C01B 32/50* (2017.08); *B01D 2256/16* (2013.01); *B01D 2256/22* (2013.01); *B01D 2257/502* (2013.01); *B01D 2257/504* (2013.01); *B01D 2257/7025* (2013.01);
(Continued)

(58) Field of Classification Search
CPC .................... B01D 2256/16; B01D 2257/7025
See application file for complete search history.

(56) References Cited

U.S. PATENT DOCUMENTS 4,381,418 A * 4/1983 Gewartowski .......... C07C 5/333 585/654
5,785,739 A * 7/1998 Baker .................. B01D 53/229 95/266
(Continued)

FOREIGN PATENT DOCUMENTS

EP 3922621 B1 * 8/2023 ............. C07C 11/04
WO WO-2022150263 A1 * 7/2022 ............... C10G 9/36
(Continued)

OTHER PUBLICATIONS

Machine Translation of EP-3922621-B1 (Year: 2023).*
(Continued)

*Primary Examiner* — Ellen M Mcavoy
*Assistant Examiner* — Ming Cheung Po

(57) ABSTRACT

Integrated steam cracking processes and hydrogen production processes are described. The steam cracker off gas stream and the synthesis gas stream are sent to the separation zone of the hydrogen production process and separated into a hydrogen stream, a carbon dioxide stream, and a second off gas stream in a separation zone. The second off gas stream comprises methane from the synthesis gas and methane from the steam cracker off gas stream, as well as carbon monoxide from the synthesis gas stream. All or a portion of the hydrogen product stream is sent to the steam cracking zone as fuel for the steam cracker reactor. The remainder (if any) of the hydrogen product stream can be recovered. The second off gas stream is sent to the hydrogen production zone as feed for the synthesis gas reactor. The carbon dioxide can be recovered.

20 Claims, 4 Drawing Sheets

(51) Int. Cl.

| | |
|---|---|
| ***B01D 53/047*** | (2006.01) |
| ***B01D 53/22*** | (2006.01) |
| ***B01D 53/26*** | (2006.01) |
| ***C01B 3/24*** | (2006.01) |
| ***C01B 3/36*** | (2006.01) |
| ***C01B 3/48*** | (2006.01) |
| ***C01B 3/501*** | (2026.01) |
| ***C01B 3/506*** | (2026.01) |
| ***C01B 3/56*** | (2006.01) |
| ***C01B 32/50*** | (2017.01) |

(52) U.S. Cl.

CPC .... *B01D 2257/80* (2013.01); *C01B 2203/025* (2013.01); *C01B 2203/0266* (2013.01); *C01B 2203/0283* (2013.01); *C01B 2203/041* (2013.01); *C01B 2203/043* (2013.01); *C01B 2203/046* (2013.01); *C01B 2203/047* (2013.01); *C01B 2203/0475* (2013.01); *C01B 2203/048* (2013.01); *C01B 2203/0495* (2013.01); *C01B 2203/062* (2013.01); *C01B 2203/1235* (2013.01); *C01B 2203/147* (2013.01); *C01B 2203/148* (2013.01)

(56) References Cited

U.S. PATENT DOCUMENTS

| | | | | |
|---|---|---|---|---|
| 8,507,742 | B2 * | 8/2013 | Chewter .................. | C10G 3/52 585/650 |
| 10,676,681 | B2 | 6/2020 | Ward et al. | |
| 2010/0288123 | A1 * | 11/2010 | Chen ........................ | C01B 3/501 95/93 |
| 2020/0101411 | A1 | 4/2020 | Russell | |
| 2021/0277318 | A1 | 9/2021 | Harale et al. | |
| 2023/0287284 | A1 * | 9/2023 | Jones ...................... | C10G 47/22 |

FOREIGN PATENT DOCUMENTS

| | | | | |
|---|---|---|---|---|
| WO | WO-2022171906 | A2 * | 8/2022 | ............. C10K 3/026 |
| WO | 2023034057 | A1 | 3/2023 | |

OTHER PUBLICATIONS

International Search Report from corresponding PCT application No. PCT/US2024/056037, mailed Mar. 7, 2025.

Written Opinion from corresponding PCT application No. PCT/US2024/056037, mailed Mar. 7, 2025.

* cited by examiner

INTEGRATED STEAM CRACKING AND HYDROGEN PRODUCTION PROCESS

BACKGROUND

There is current interest in decarbonization of steam cracker plants for producing low-carbon ethylene. One approach is fuel switching to blue hydrogen. Methane recovered from steam cracker off gas can be used as feedstock in the blue hydrogen plant, along with supplemental natural gas. The current flow scheme (especially for ethane crackers) requires a stand-alone separation block for separating hydrogen and methane from the steam cracker off gas. The recovered hydrogen is used as fuel gas, while the recovered methane is feedstock for the blue hydrogen process.

For example, WO 2023/034057 describes a process for producing decarbonized blue hydrogen gas for cracking operations. The process includes a standard separation process, such as pressure swing adsorption (PSA) to separate the tail gas mixture of hydrogen and hydrocarbons from the steam cracker into hydrogen gas and a PSA effluent that is used in a hydrogen generation unit to produce the decarbonized blue hydrogen gas for cracking operations. Blue hydrogen is hydrogen that is produced from fossil fuel feedstocks (such as natural gas, LPG, or naphtha) where the carbon dioxide byproduct from the production process is captured and geologically sequestered or utilized.

FIG. 1 illustrates one example of a prior art combined steam cracker and hydrogen generation process. The hydrocarbon feed 105 (e.g., ethane) is processed in a steam cracking zone 110 and separated into an ethylene stream 115, and a steam cracking off gas stream 120 containing hydrogen and methane. The steam cracking off gas stream 120 is sent to a first separation unit 125 which forms a hydrogen stream 130 and an effluent stream 135 containing methane and some hydrogen. The effluent stream 135 is sent to a hydrogen production zone 140 along with a hydrocarbon feed stream 145 (e.g., natural gas) and optionally oxygen 150, depending on the type of hydrogen production zone. The hydrogen production zone 140 produces a synthesis gas stream 155 comprising hydrogen, carbon dioxide, carbon monoxide and methane. The synthesis gas stream 155 is sent to a second separation unit 160 where it is separated into a hydrogen stream 165, a carbon dioxide stream 170, and a recycle stream 175 comprising methane and carbon monoxide. The hydrogen stream 165 from the second separation unit 160 is combined with the hydrogen stream 130 from the first separation unit 125 and sent to the steam cracking zone 110 as fuel. The recycle stream 175 which contains methane and carbon monoxide is sent to the hydrogen production zone 140 as feed. The carbon dioxide stream 170 is recovered.

A disadvantage of this process is that two separation units are required: the first separation unit 125 for the steam cracker off gas 120 and the second separation unit 160 for the synthesis gas stream 155 from the hydrogen production unit 140. The separation units are expensive, requiring multiple compressors and one or more membrane and/or PSA units.

Therefore, there is a need for a less expensive process for integrated steam cracking and blue hydrogen production.

DESCRIPTION

The present invention meets this need by eliminating the stand-alone separation block by integrating the methane/hydrogen separation into the separation section of the blue hydrogen plant, thereby reducing equipment count and capital cost. As described below, this integration also provides synergies to reduce overall power consumption that cannot be realized with the stand-alone separation units in the prior art.

The processes involve steam cracking processes combined with hydrogen production processes. The steam cracking process typically involves cracking a feed stream comprising hydrocarbons (such as ethane or naphtha) in the presence of steam to produce alkenes, such as ethylene. The steam cracking process also produces a steam cracker off gas stream comprising hydrogen and methane. The hydrogen production process produces synthesis gas comprising hydrogen, carbon dioxide, methane, and carbon monoxide in a hydrogen production zone. The synthesis gas from the hydrogen production zone and the steam cracker off gas stream from the steam cracking zone are separated into a hydrogen stream, a carbon dioxide stream, and a second off gas stream in a separation zone. The second off gas stream comprises methane and carbon monoxide from the synthesis gas and hydrogen and methane from the steam cracker off gas stream. All or a portion of the hydrogen product stream is sent to the steam cracking zone as fuel for the steam cracker reactor. The remainder (if any) of the hydrogen product stream can be recovered. The second off gas stream is sent to the hydrogen production zone as feed for the synthesis gas reactor. The carbon dioxide can be recovered.

The hydrogen production zone comprises a synthesis gas reactor. Any suitable synthesis gas reactor can be used, including, but not limited to, steam methane reformers, autothermal reformers, partial oxidation reactors, gasification reactors, or combinations thereof. The synthesis gas reactor produces an effluent which comprises a mixture of gases comprising hydrogen, carbon dioxide, water, and at least one of carbon monoxide, methane, nitrogen, and argon. The hydrogen production zone typically includes a water gas shift unit to convert carbon monoxide to carbon dioxide and hydrogen.

The separation zone comprises a hydrogen separation unit and a carbon dioxide separation unit. Any suitable hydrogen separation can be used, including, but not limited to, pressure swing adsorption units, membrane separation units, or combinations thereof. Any suitable carbon dioxide separation can be used, including, but not limited to, cryogenic fractionation units, solvent based units, or combinations thereof.

Figure 1:
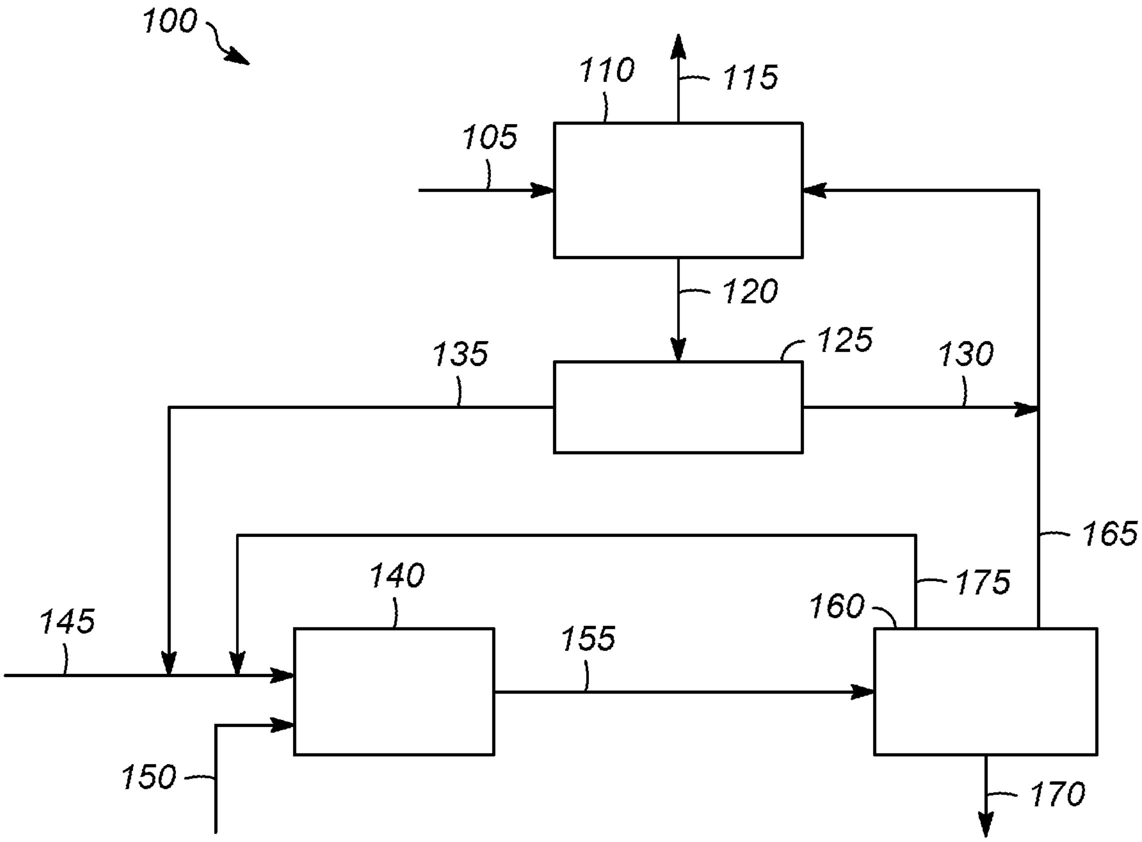
FIG. 1 illustrates an example of a prior art process for steam cracking and hydrogen production.
Figure 2:
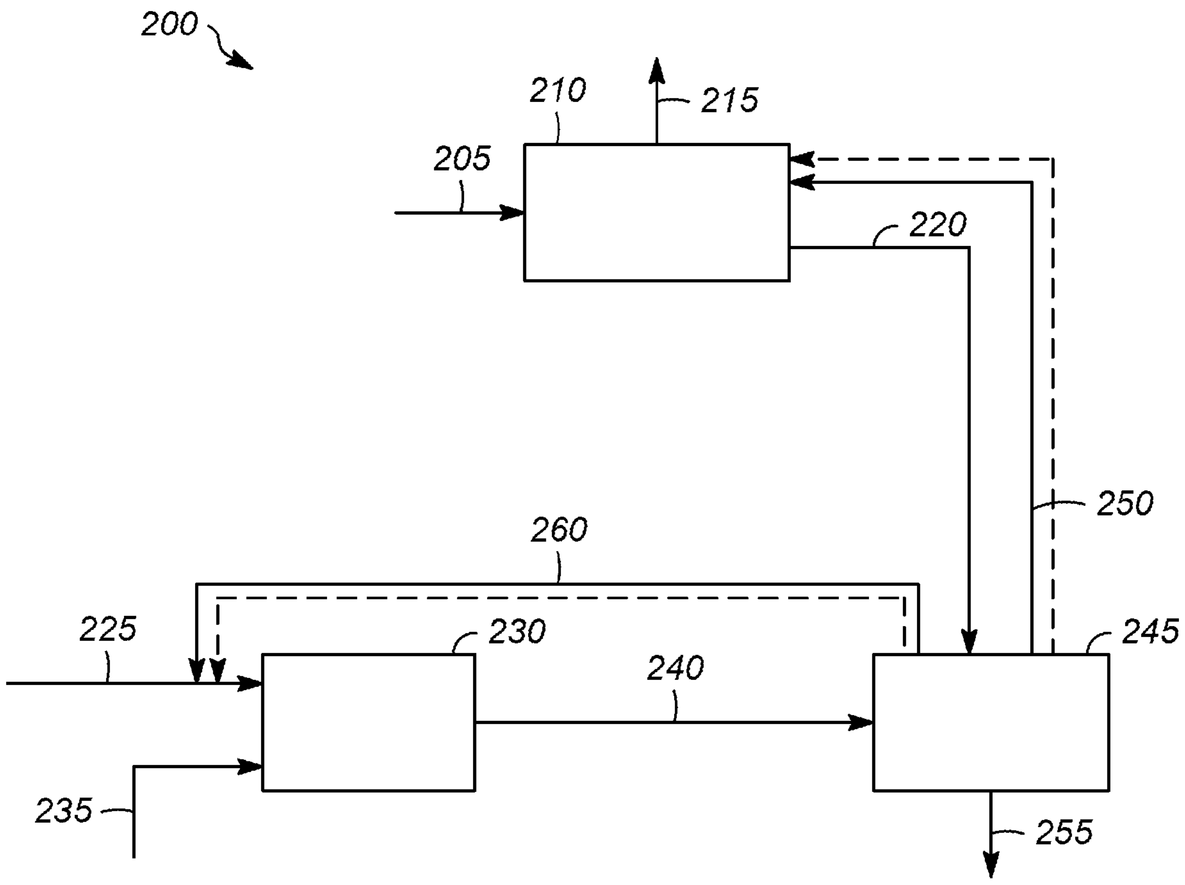
FIG. 2 illustrates one embodiment of an integrated steam cracking and hydrogen production process according to the present invention.

FIG. 2 illustrates one example of combined steam cracker and hydrogen generation process according to the present invention. The hydrocarbon feed 205 is processed in a steam cracking zone 210 comprising a steam cracking reactor and separated into an ethylene stream 215, and a steam cracking off gas stream 220 containing hydrogen and methane.

A hydrocarbon feed stream 225 is sent to a hydrogen production zone 230, optionally with oxygen 235 depending on the type of synthesis gas reactor. The hydrogen production zone 230 produces a synthesis gas stream 240 comprising hydrogen, carbon dioxide, carbon monoxide and methane.

The synthesis gas stream 240 and steam cracking off gas stream 220 are sent to a common separation zone 245 where it is separated into a hydrogen stream 250, a carbon dioxide-enriched product stream 255, and a second off gas stream 260. The hydrogen stream 250 comprises hydrogen from the synthesis gas stream 240 and hydrogen from the steam cracking off gas stream 220. The c carbon dioxide-enriched product stream 255 comprises carbon dioxide primarily from the synthesis gas stream 240. The second off gas stream 260 comprises methane from the steam cracking off gas stream 220 and methane from the synthesis gas stream 240 and carbon monoxide primarily from the synthesis gas stream 240.

The hydrogen stream 250 from the separation zone 245 is sent to the steam cracking zone 210 as fuel. The second off gas stream 260, which contains methane and carbon monoxide, is sent to the hydrogen production zone 230 as feed. The carbon dioxide-enriched product stream 255 can be recovered.

Figure 3:
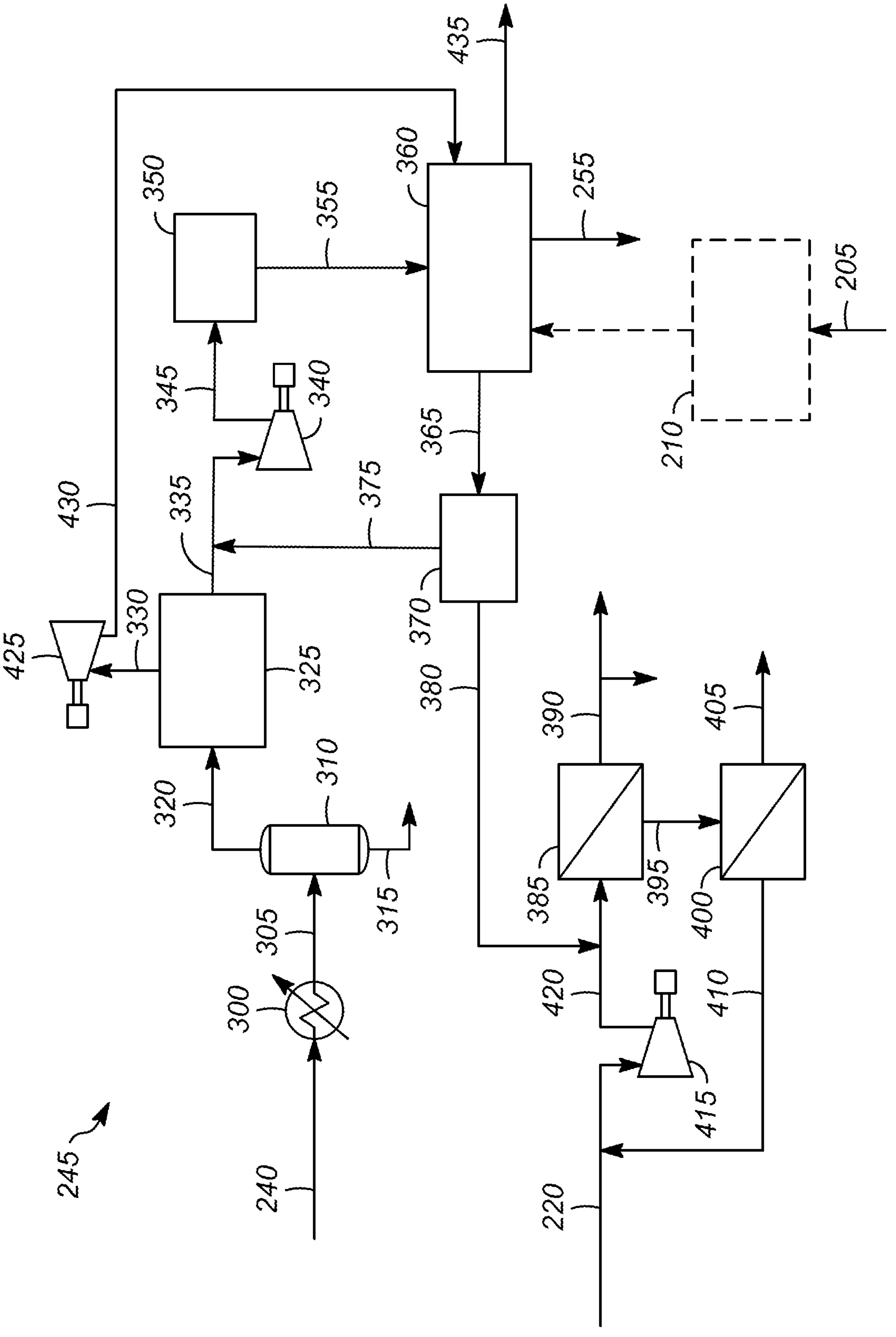
FIG. 3 illustrates one embodiment of a separation zone of an integrated steam cracking and hydrogen production process according to the present invention.

FIG. 3 illustrates one embodiment of the separation zone 245. The synthesis gas stream 240 is chilled in inlet gas chiller 300. The chilled synthesis gas stream 305, which has a temperature of about 0° C. to about 40° C., is sent to a knockout pot 310 where a water stream 315 is removed resulting in a chilled synthesis gas stream 320 having a lower level of water than the incoming chilled synthesis gas stream 305. In cases where methanol is present in the synthesis gas stream 240, a portion of the methanol will be removed with water stream 315.

The chilled synthesis gas stream 320 is sent to the hydrogen PSA unit 325 where it is separated into a high-pressure hydrogen product stream 330 and a low-pressure hydrogen-depleted tail gas stream 335.

The high-pressure hydrogen product stream 330 may have a temperature of 10 to 50° C. and a pressure of 20 to 40 bar (g), and it may contain 99.0 to 99.999 mol % hydrogen, less than 1 ppmv carbon dioxide, less than 1 ppmv to 1000 ppmv methane, less than 1 ppmv to 50 ppmv carbon monoxide, 0 to 2000 ppmv nitrogen, less than 1 ppmv water, 0 to 3000 ppmv argon, and less than 0.1 ppmv methanol.

The low-pressure hydrogen-depleted tail gas stream 335 may have a temperature of 0 to 40° C. and a pressure of 0.2 to 0.5 bar (g), and it may contain 20 to 30 mol % hydrogen, 55 to 75 mol % carbon dioxide, 2 to 15 mol % methane, 1 to 15 mol % carbon monoxide, 0 to 2 mol % nitrogen, 1 to 2 mol % water, 0 to 0.4 mol % argon, and 0 to 1000 ppmv methanol.

The low-pressure hydrogen-depleted tail gas stream 335 is compressed in compressor 340 from a pressure in the range of about 110 kPa to about 200 kPa to a pressure in the range of about 3,000 kPa to about 5,000 kPa. The compressed tail gas stream 345 is dried in drier 350, and the compressed, dried tail gas stream 355 is sent to a carbon dioxide separation unit 360.

The compressed, dried tail gas stream is separated into the carbon dioxide-enriched product stream 255 and an overhead stream 365. The carbon dioxide-enriched product stream 255 can be recovered.

The overhead stream 365 may have a temperature of 0 to 40° C. and a pressure of 3,000 kPa to 5,000 kPa, and it may contain 50 to 80 mol % hydrogen, 10 to 20 mol % carbon dioxide, 5 to 20 mol % methane, 5 to 20 mol % carbon monoxide, 0 to 20 mol % nitrogen, and 0 to 1 mol % argon.

The overhead stream 365 is sent to a second PSA unit 370 to form a low-pressure carbon dioxide stream 375 enriched in carbon dioxide and a third off-gas stream 380 enriched in hydrogen and at least one of carbon monoxide, methane, nitrogen, and argon.

The low-pressure carbon dioxide stream 375 may have a temperature of 0 to 30° C. and a pressure of 0.2 to 0.5 bar (g), and it may contain 10 to 20 mol % hydrogen, 60 to 80 mol % carbon dioxide, 2 to 10 mol % methane, 2 to 10 mol % carbon monoxide, 0 to 10 mol % nitrogen, and 0 to 0.5 mol % argon. The third off-gas stream 380 may have a temperature of 30 to 40° C. and a pressure of 3,000 kPa to 5,000 kPa, and it may contain 50 to 90 mol % hydrogen, 0.01 to 0.5 mol % carbon dioxide, 5 to 30 mol % methane, 5 to 30 mol % carbon monoxide, 0 to 20 mol % nitrogen, and 0 to 1 mol % argon.

A steam cracking off gas stream 220 comprising hydrogen and methane is compressed in compressor 415 to form compressed off gas stream 420. The steam cracking off gas stream 220 may have a temperature of 10 to 40° C. and a pressure of 300 kPa to 1,000 kPa, and it may contain 60 to 90 mol % hydrogen, 10 to 30 mol % methane, 0.1 to 0.3 mol % ethylene, and 0.05 to 0.2 mol % carbon monoxide.

The third off gas stream 380 is mixed with compressed off gas stream 420 and is sent to a first membrane separation unit 385 where it is separated into a first permeate stream 390 comprising hydrogen and a first retentate stream 395 comprising carbon monoxide and methane. The first permeate stream 390 can be sent to the steam cracking zone 210 as fuel, to the hydrogen production zone 230 as fuel, and/or recovered as hydrogen product.

The first retentate stream 395 is sent to a second membrane separation unit 400 where it is separated into second retentate stream 405 comprising methane and carbon monoxide and a second permeate stream 410 comprising hydrogen. The second retentate stream 405 can be sent to the hydrogen production zone 230 as feed.

The second permeate stream 410 is mixed with steam cracking off gas stream 220 and compressed in compressor 415, and the compressed off gas stream 420 is sent to the first membrane separation unit 385.

The high-pressure hydrogen product stream 330 from the hydrogen PSA unit 325 is expanded in expander 425 forming a chilled hydrogen product stream 430 which is sent to the carbon dioxide separation unit 360. The hydrogen product stream 435 can be sent to the steam cracking zone 210 as fuel or to the hydrogen production zone 230 as fuel or recovered.

Figure 4:
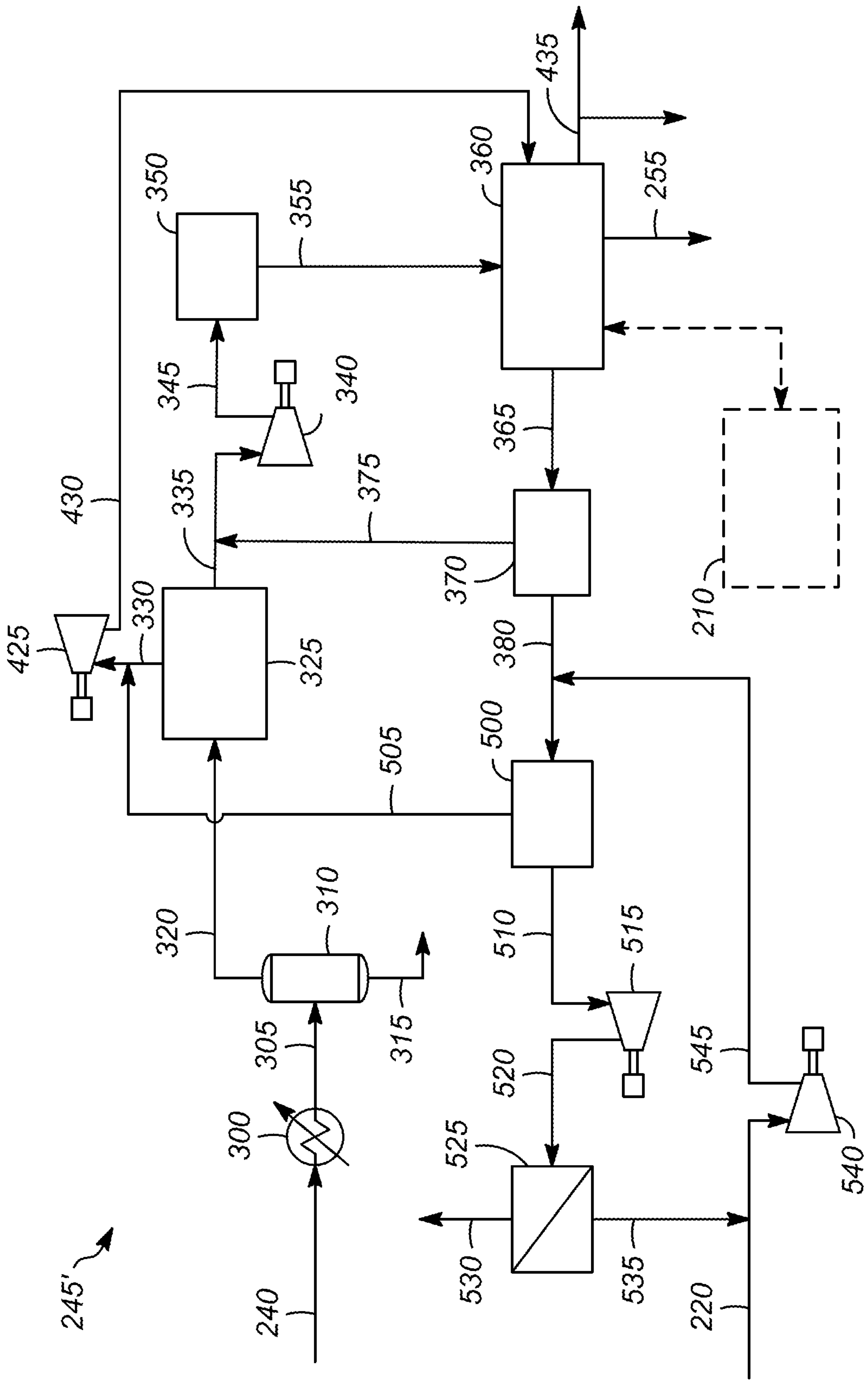
FIG. 4 illustrates another embodiment of a separation zone of an integrated steam cracking and hydrogen production process according to the present invention.

FIG. 4 illustrates another embodiment of the separation zone 245'. The synthesis gas stream 240 is chilled in inlet gas chiller 300. The chilled synthesis gas stream 305, which has a temperature of about 0° C. to about 40° C., is sent to a knockout pot 310 where a water stream 315 is removed resulting in a chilled synthesis gas stream 320 having a lower level of water than the incoming chilled synthesis gas stream 305. In cases where methanol is present in the synthesis gas stream 240, a portion of the methanol will be removed with water stream 315.

The chilled synthesis gas stream 320 is sent to the hydrogen PSA unit 325 where it is separated into a high-pressure hydrogen product stream 330 and a low-pressure hydrogen-depleted tail gas stream 335.

The high-pressure hydrogen product stream 330 may have a temperature of 10 to 50° C. and a pressure of 20 to 40 bar (g), and it may contain 99.0 to 99.999 mol % hydrogen, less than 1 ppmv carbon dioxide, less than 1 ppmv to 1000 ppmv methane, less than 1 ppmv to 50 ppmv carbon monoxide, 0 to 2000 ppmv nitrogen, less than 1 ppmv water, 0 to 3000 ppmv argon, and less than 0.1 ppmv methanol.

The low-pressure hydrogen-depleted tail gas stream 335 may have a temperature of 0 to 40° C. and a pressure of 0.2 to 0.5 bar (g), and it may contain 20 to 30 mol % hydrogen, 55 to 75 mol % carbon dioxide, 2 to 15 mol % methane, 1 to 15 mol % carbon monoxide, 0 to 2 mol % nitrogen, 1 to 2 mol % water, 0 to 0.4 mol % argon, and 0 to 1000 ppmv methanol.

The low-pressure hydrogen-depleted tail gas stream 335 is compressed in compressor 340 from a pressure in the range of about 110 kPa to about 200 kPa to a pressure in the range of about 3,000 kPa to about 5,000 kPa. The compressed tail gas stream 345 is dried in drier 350, and the compressed, dried tail gas stream 355 is sent to a carbon dioxide separation unit 360.

The compressed, dried tail gas stream is separated into the carbon dioxide-enriched product stream 255 and an overhead stream 365. The carbon dioxide-enriched product stream 255 can be recovered.

The overhead stream 365 may have a temperature of 20 to 40° C. and a pressure of 3,000 to 5,000 kPa, and it may contain 50 to 80 mol % hydrogen, 10 to 20 mol % carbon dioxide, 5 to 20 mol % methane, 5 to 20 mol % carbon monoxide, 0 to 20 mol % nitrogen, and 0 to 1 mol % argon.

The overhead stream 365 is sent to a second PSA unit 370 to form a low-pressure carbon dioxide stream 375 enriched in carbon dioxide and a third off-gas stream 380 enriched in hydrogen and at least one of carbon monoxide, methane, nitrogen, and argon.

The low-pressure carbon dioxide stream 375 may have a temperature of 0 to 30° C. and a pressure of 0.2 to 0.5 bar (g), and it may contain 10 to 20 mol % hydrogen, 60 to 80 mol % carbon dioxide, 2 to 10 mol % methane, 2 to 10 mol % carbon monoxide, 0 to 10 mol % nitrogen, and 0 to 0.5 mol % argon. The third off-gas stream 380 may have a temperature of 30 to 40° C. and a pressure of 3,000 to 5,000 kPa, and it may contain 50 to 90 mol % hydrogen, 0.01 to 0.5 mol % carbon dioxide, 5 to 30 mol % methane, 5 to 30 mol % carbon monoxide, 0 to 20 mol % nitrogen, and 0 to 1 mol % argon.

A steam cracking off gas stream 220 comprising hydrogen and methane is compressed in compressor 540 to form compressed off gas stream 545. The steam cracking off gas stream 220 may have a temperature of 10 to 40° C. and a pressure of 300 kPa to 1000 kPa, and it may contain 60 to 90 mol % hydrogen, 10 to 30 mol % methane, 0.1 to 0.3 mol % ethylene, and 0.05 to 0.2 mol % carbon monoxide.

The third off gas stream 380 is mixed with compressed off gas stream 545 and sent to a third PSA unit 500 where it is separated into a second hydrogen product stream 505 and a second tail gas stream 510. The second tail gas stream 510 is compressed in compressor 515, and the compressed second tail gas stream 520 is sent to a membrane separation unit 525 where it is separated into a retentate stream 530 comprising methane and carbon monoxide and a permeate stream 535 comprising hydrogen.

The retentate stream 530 can be sent to the hydrogen production zone 230 as feed.

The permeate stream 535 is mixed with steam cracking off gas stream 220 and sent to compressor 540, and the compressed off gas stream 545 is sent to the third PSA unit 500.

The high-pressure hydrogen product stream 330 from the hydrogen PSA unit 325 and the second hydrogen product stream 505 from the third PSA unit 500 are expanded in expander 425 forming a chilled hydrogen product stream 430 which is sent to the carbon dioxide separation unit 360. The hydrogen product stream 435 can be sent to the steam cracking zone 210 as fuel or to the hydrogen production zone 230 as fuel or recovered.

EXAMPLES

A computer simulation was conducted for the flow scheme in FIG. 4. A material balance is given below in Table 1. This example represents an ethane steam cracker and an autothermal reforming hydrogen production process. Feedstock for the autothermal reforming hydrogen production process comprises natural gas and retentate stream 530. The carbon dioxide separation unit 360 is comprised of a cryogenic fractionation system.

The synergy achieved by integrating the steam cracker off-gas separation into the separation section of the hydrogen production zone includes: power recovery in expander 425 and chilling recovery from the chilled hydrogen product stream 430. The power recovered in expander 425 decreases the net power import requirement for the process by 18%, and the chilling recovered from the chilled hydrogen product stream 430 provides 34% of the chilling duty for the process.

TABLE 1

| | Steam Cracker Off Gas | 240 Shifted Syngas | 435 Combined H2 Product | 255 Product CO2 | 530 Membrane Retentate | 505 H2 Product from PSA 500 |
|---|---|---|---|---|---|---|
| Molar Flow, MMSCFD | 231.4 | 219.1 | 341.6 | 52.86 | 53.09 | 197.4 |
| Pressure, psig | 78 | 313 | 90 | 2205 | 435 | 295 |
| Temp. ° F. | 95 | 104 | 50 | 84 | 140 | 120 |
| Composition, mol % | | | | | | |
| H2 | 80.45 | 72.23 | 98.48 | 0.00 | 15.05 | 98.66 |
| CO | 0.11 | 0.46 | 0.03 | 0.03 | 2.11 | 30 ppmv |
| CO2 | 0.00 | 24.05 | <10 ppmv | 99.59 | 0.07 | <10 ppmv |
| Methane | 16.66 | 0.57 | 0.02 | 0.34 | 74.54 | 260 ppmv |
| N2 | 1.68 | 2.25 | 1.45 | 0.03 | 7.29 | 1.30 |
| Argon | 0.00 | 390 ppmv | 210 ppmv | 0.01 | 0.02 | 70 ppmv |
| Ethylene | 0.20 | 0.00 | 0.00 | 0.00 | 0.85 | 0.00 |
| Water | 0.90 | 0.40 | 0.00 | <50 ppmv | 0.07 | 0.00 |

TABLE 1-continued

| | Steam Cracker Off Gas | 240 Shifted Syngas | 435 Combined H2 Product | 255 Product CO2 | 530 Membrane Retentate | 505 H2 Product from PSA 500 |
|---|---|---|---|---|---|---|
| Total | 100.00 | 100.00 | 100.00 | 100.00 | 100.00 | 100.00 |

SPECIFIC EMBODIMENTS

While the following is described in conjunction with specific embodiments, it will be understood that this description is intended to illustrate and not limit the scope of the preceding description and the appended claims.

A first embodiment of the invention is a process for producing ethylene and hydrogen comprising producing an ethylene product stream and a steam cracker off gas stream comprising hydrogen and methane in a steam cracking zone comprising a steam cracking reactor; producing a synthesis gas stream comprising hydrogen, methane, carbon monoxide, and carbon dioxide in a hydrogen production zone comprising a synthesis gas reactor and a separation zone comprising a hydrogen separation unit and a carbon dioxide separation unit; separating the synthesis gas stream and the steam cracker off gas stream in the separation zone of the hydrogen production zone producing a hydrogen product stream comprising hydrogen from the synthesis gas stream and hydrogen from the steam cracker off gas stream, a carbon dioxide product stream comprising carbon dioxide, and a second off gas stream comprising methane from the steam cracker off gas stream and methane from the synthesis gas stream and carbon monoxide from the synthesis gas stream; passing the hydrogen product stream to the steam cracking zone as fuel gas; passing the second off gas stream from the separation zone to the hydrogen production zone; and recovering the carbon dioxide product stream. An embodiment of the invention is one, any or all of prior embodiments in this paragraph up through the first embodiment in this paragraph wherein the hydrogen separation unit comprises a pressure swing adsorption unit, a membrane separation unit, or combinations thereof. An embodiment of the invention is one, any or all of prior embodiments in this paragraph up through the first embodiment in this paragraph wherein the carbon dioxide separation unit comprises a cryogenic fractionation unit, a solvent based unit, or combinations thereof. An embodiment of the invention is one, any or all of prior embodiments in this paragraph up through the first embodiment in this paragraph wherein sending the hydrogen product stream to the steam cracking zone comprises sending a first portion of the hydrogen product stream to the steam cracking zone, and further comprising recovering a second portion of the hydrogen product stream. An embodiment of the invention is one, any or all of prior embodiments in this paragraph up through the first embodiment in this paragraph wherein separating the synthesis gas stream and the steam cracker off gas stream in the separation zone of the hydrogen production zone comprises separating the synthesis gas stream in the hydrogen separation unit to form a hydrogen product stream enriched in hydrogen and a hydrogen-depleted tail gas stream; compressing the hydrogen-depleted tail gas stream in a tail gas compressor to form a compressed tail gas stream; drying the compressed tail gas stream to form a dried compressed tail gas stream; separating the compressed tail gas stream in the carbon dioxide separation unit to form the carbon dioxide-enriched product stream and an overhead stream; separating the overhead stream in a second PSA unit to form a low-pressure carbon dioxide stream enriched in carbon dioxide and a third off-gas stream enriched in hydrogen, and carbon monoxide or methane or both; mixing the steam cracker off gas stream with the third off-gas stream to form a fourth off-gas stream; recycling the low-pressure carbon dioxide stream to the tail gas compressor; and introducing the fourth off-gas stream to the hydrogen production zone. An embodiment of the invention is one, any or all of prior embodiments in this paragraph up through the first embodiment in this paragraph wherein introducing the fourth off-gas stream to the hydrogen production zone comprises separating the fourth off-gas stream in a first membrane separation unit forming a first permeate stream comprising hydrogen and a first retentate stream comprising the carbon monoxide or the methane or both; and introducing the first retentate stream into the hydrogen production zone. An embodiment of the invention is one, any or all of prior embodiments in this paragraph up through the first embodiment in this paragraph further comprising separating the first retentate stream in a second membrane separation unit into a second retentate stream comprising the carbon monoxide or the methane or both and a second permeate stream comprising hydrogen; compressing the second permeate stream in a second compressor forming a compressed permeate stream; introducing the compressed permeate stream into the first membrane separation unit; and introducing the second retentate stream into the hydrogen production zone. An embodiment of the invention is one, any or all of prior embodiments in this paragraph up through the first embodiment in this paragraph further comprising compressing the steam cracker off gas stream in the second compressor forming a compressed steam cracker off gas stream; introducing the compressed steam cracker off gas stream into the first membrane separation unit. An embodiment of the invention is one, any or all of prior embodiments in this paragraph up through the first embodiment in this paragraph further comprising expanding the hydrogen product stream to form a chilled hydrogen product stream; recovering power from the expander; chilling at least one stream in the separation zone of the hydrogen production zone with the chilled hydrogen stream forming a warm hydrogen stream; recovering the warm hydrogen stream. An embodiment of the invention is one, any or all of prior embodiments in this paragraph up through the first embodiment in this paragraph wherein introducing the fourth off-gas stream to the hydrogen production zone comprises separating the fourth off-gas stream in a third PSA unit into a second hydrogen product stream and a second tail gas stream comprising carbon monoxide or methane or both; compressing the second tail gas stream in a second tail gas compressor forming a second compressed tail gas stream; separating the second compressed tail gas stream in a membrane separation unit into a retentate stream comprising the carbon monoxide or the methane or both and a permeate stream comprising hydrogen; compressing the permeate stream in a permeate compressor forming a compressed permeate stream; introducing the compressed permeate stream into the third PSA unit. An embodiment of the invention is one, any or all of prior embodiments in this paragraph up through the first embodiment in this paragraph further comprising; introducing the steam cracker off-gas stream into the permeate compressor. An embodiment of the invention is one, any or all of prior embodiments in this paragraph up through the first embodiment in this paragraph further comprising combining the first hydrogen product stream and the second hydrogen product stream. An embodiment of the invention is one, any or all of prior embodiments in this paragraph up through the first embodiment in this paragraph wherein the hydrogen separation unit comprises a hydrogen pressure swing adsorption (PSA) unit and wherein the carbon dioxide separation unit comprises a cryogenic separation unit. An embodiment of the invention is one, any or all of prior embodiments in this paragraph up through the first embodiment in this paragraph wherein the synthesis gas reactor comprises a steam methane reformer, an autothermal reformer, a partial oxidation reactor, a gasification reactor, or combinations thereof. An embodiment of the invention is one, any or all of prior embodiments in this paragraph up through the first embodiment in this paragraph wherein the hydrogen production zone further comprises a water gas shift reactor.

A second embodiment of the invention is a process for producing ethylene and hydrogen comprising producing an ethylene product stream and a steam cracker off gas stream comprising hydrogen and methane in a steam cracking zone comprising a steam cracking reactor; producing a synthesis gas stream comprising hydrogen, methane, carbon monoxide, and carbon dioxide in a hydrogen production zone comprising a synthesis gas reactor and a separation zone comprising a hydrogen separation unit and a carbon dioxide separation unit, wherein the hydrogen separation unit comprises a pressure swing adsorption unit, a membrane separation unit, or combinations thereof, or wherein the carbon dioxide separation unit comprises a cryogenic fractionation unit, a solvent based unit, or combinations thereof, or both; separating the synthesis gas stream and the steam cracker off gas stream in the separation zone of the hydrogen production zone producing a hydrogen product stream comprising hydrogen from the synthesis gas stream and hydrogen from the steam cracker off gas stream, a carbon dioxide product stream comprising carbon dioxide, and a second off gas stream comprising methane from the steam cracker off gas stream and methane from the synthesis gas stream and carbon monoxide from the synthesis gas stream; passing the hydrogen product stream to the steam cracking zone as fuel gas; passing the second off gas stream from the separation zone to the hydrogen production zone; and recovering the carbon dioxide product stream; expanding the hydrogen product stream to form a chilled hydrogen product stream; recovering power from the expander; chilling at least one stream in the separation zone of the hydrogen production zone with the chilled hydrogen stream forming a warm hydrogen stream; recovering the warm hydrogen stream. An embodiment of the invention is one, any or all of prior embodiments in this paragraph up through the second embodiment in this paragraph wherein separating the synthesis gas stream and the steam cracker off gas stream in the separation zone of the hydrogen production zone comprises separating the synthesis gas stream in the hydrogen separation unit to form a hydrogen product stream enriched in hydrogen and a hydrogen-depleted tail gas stream; compressing the hydrogen-depleted tail gas stream in a tail gas compressor to form a compressed tail gas stream; drying the compressed tail gas stream to form a dried compressed tail gas stream; separating the compressed tail gas stream in the carbon dioxide separation unit to form the carbon dioxide-enriched product stream and an overhead stream; separating the overhead stream in a second PSA unit to form a low-pressure carbon dioxide stream enriched in carbon dioxide and a third off-gas stream enriched in hydrogen, and carbon monoxide or methane or both; mixing the steam cracker off gas stream with the third off-gas stream to form a fourth off-gas stream; recycling the low-pressure carbon dioxide stream to the tail gas compressor; and introducing the fourth off-gas stream to the hydrogen production zone. An embodiment of the invention is one, any or all of prior embodiments in this paragraph up through the second embodiment in this paragraph wherein introducing the fourth off-gas stream to the hydrogen production zone comprises separating the fourth off-gas stream in a first membrane separation unit forming a first permeate stream comprising hydrogen and a first retentate stream comprising the carbon monoxide or the methane or both; introducing the first retentate stream into the hydrogen production unit. An embodiment of the invention is one, any or all of prior embodiments in this paragraph up through the second embodiment in this paragraph further comprising separating the first retentate stream in a second membrane separation unit into a second retentate stream comprising the carbon monoxide or the methane or both and a second permeate stream comprising hydrogen; compressing the second permeate stream in a second compressor forming a compressed second permeate stream; and introducing the compressed second permeate stream into the first membrane separation unit; or compressing the steam cracker off gas stream in the compressor forming a compressed steam cracker off gas stream; and introducing the compressed steam cracker off gas stream into the first membrane separation unit; or both An embodiment of the invention is one, any or all of prior embodiments in this paragraph up through the second embodiment in this paragraph wherein introducing the fourth off-gas stream to the hydrogen production zone comprises separating the fourth off-gas stream in a third PSA unit into a second hydrogen product stream and a second tail gas stream comprising carbon monoxide or methane or both; compressing the second tail gas stream in a second tail gas compressor forming a second compressed tail gas stream; separating the second compressed tail gas stream in a membrane separation unit into a first retentate stream comprising the carbon monoxide or the methane or both and a first permeate stream comprising hydrogen; compressing the first permeate stream in a permeate compressor forming a compressed first permeate stream; introducing the compressed first permeate stream into the third PSA unit.

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

What is claimed is:

1. An integrated process for producing ethylene and hydrogen comprising:

producing an ethylene product stream and a steam cracker off gas stream comprising hydrogen and methane in a steam cracking zone comprising a steam cracking reactor;

producing a synthesis gas stream comprising hydrogen, methane, carbon monoxide, and carbon dioxide in a hydrogen production zone comprising a synthesis gas reactor;

passing the synthesis gas stream from the hydrogen production zone and the steam cracker off gas stream from the steam cracking zone to a common separation zone comprising a hydrogen separation unit and a carbon dioxide separation unit and separating the synthesis gas stream and the steam cracker off gas stream into a hydrogen product stream comprising hydrogen from the synthesis gas stream and hydrogen from the steam cracker off gas stream, a carbon dioxide product stream comprising carbon dioxide, and a second off gas stream comprising methane from the steam cracker off gas stream and methane from the synthesis gas stream and carbon monoxide from the synthesis gas stream;

passing the hydrogen product stream to the steam cracking zone as fuel gas;

passing the second off gas stream from the common separation zone to the hydrogen production zone; and recovering the carbon dioxide product stream, wherein separating the synthesis gas stream and the steam cracker off gas stream further comprises:

separating the synthesis gas stream in the hydrogen separation unit to form a hydrogen product stream enriched in hydrogen and a hydrogen-depleted tail gas stream;

separating the hydrogen-depleted tail gas stream in the carbon dioxide separation unit to form the carbon dioxide-enriched product stream and an overhead stream;

separating the overhead stream in a second PSA unit to form a low-pressure carbon dioxide stream enriched in carbon dioxide and a third off-gas stream enriched in hydrogen and carbon monoxide or methane or both;

mixing the steam cracker off gas stream with the third off-gas stream to form a fourth off-gas stream; and introducing the fourth off-gas stream to the hydrogen production zone.

2. The process of claim 1 wherein the hydrogen separation unit comprises a pressure swing adsorption unit, a membrane separation unit, or combinations thereof.

3. The process of claim 1 wherein the carbon dioxide separation unit comprises a cryogenic fractionation unit, a solvent based unit, or combinations thereof.

4. The process of claim 1 wherein passing the hydrogen product stream to the steam cracking zone comprises passing a first portion of the hydrogen product stream to the steam cracking zone, and further comprising:

recovering a second portion of the hydrogen product stream.

5. The process of claim 1 wherein separating the synthesis gas stream and the steam cracker off gas stream comprises:

compressing the hydrogen-depleted tail gas stream in a tail gas compressor to form a compressed tail gas stream;

drying the compressed tail gas stream to form a dried compressed tail gas stream; and recycling the low-pressure carbon dioxide stream to the tail gas compressor, wherein separating the hydrogen-depleted tail gas stream in the carbon dioxide separation unit comprises separating the dried compressed tail gas stream.

6. The process of claim 5 wherein introducing the fourth off-gas stream to the hydrogen production zone comprises:

separating the fourth off-gas stream in a first membrane separation unit forming a first permeate stream comprising hydrogen and a first retentate stream comprising the carbon monoxide or the methane or both; and introducing the first retentate stream into the hydrogen production zone.

7. The process of claim 6 further comprising:

separating the first retentate stream in a second membrane separation unit into a second retentate stream comprising the carbon monoxide or the methane or both and a second permeate stream comprising hydrogen;

compressing the second permeate stream in a second compressor forming a compressed permeate stream;

introducing the compressed permeate stream into the first membrane separation unit; and introducing the second retentate stream into the hydrogen production zone.

8. The process of claim 7 further comprising:

compressing the steam cracker off gas stream in the second compressor forming a compressed steam cracker off gas stream; and introducing the compressed steam cracker off gas stream into the first membrane separation unit.

9. The process of claim 1 further comprising:

expanding the hydrogen product stream to form a chilled hydrogen product stream;

recovering power from the expander;

chilling at least one stream in the separation zone with the chilled hydrogen stream forming a warm hydrogen stream; and recovering the warm hydrogen stream.

10. The process of claim 5 wherein introducing the fourth off-gas stream to the hydrogen production zone comprises:

separating the fourth off-gas stream in a third PSA unit into a second hydrogen product stream and a second tail gas stream comprising carbon monoxide or methane or both;

compressing the second tail gas stream in a second tail gas compressor forming a second compressed tail gas stream;

separating the second compressed tail gas stream in a membrane separation unit into a retentate stream comprising the carbon monoxide or the methane or both and a permeate stream comprising hydrogen;

compressing the permeate stream in a permeate compressor forming a compressed permeate stream; and introducing the compressed permeate stream into the third PSA unit.

11. The process of claim 10 further comprising;

introducing the steam cracker off-gas stream into the permeate compressor.

12. The process of claim 10 further comprising:

combining the first hydrogen product stream and the second hydrogen product stream.

13. The process of claim 1 wherein the hydrogen separation unit comprises a hydrogen pressure swing adsorption (PSA) unit and wherein the carbon dioxide separation unit comprises a cryogenic separation unit.

14. The process of claim 1 wherein the synthesis gas reactor comprises a steam methane reformer, an autothermal reformer, a partial oxidation reactor, a gasification reactor, or combinations thereof.

15. The process of claim 1 wherein the hydrogen production zone further comprises a water gas shift reactor.

16. An integrated process for producing ethylene and hydrogen comprising:

introducing a first feed hydrocarbon stream to a steam cracking zone comprising a steam cracking reactor to produce an ethylene product stream and a steam cracker off gas stream comprising hydrogen and methane;

introducing a second hydrocarbon feed stream to a hydrogen production zone comprising a synthesis gas reactor to produce synthesis gas stream comprising hydrogen, methane, carbon monoxide, and carbon dioxide;

passing the synthesis gas stream from the hydrogen production zone and the steam cracker off gas stream from the steam cracking zone to a common separation zone comprising a hydrogen separation unit and a carbon dioxide separation unit and separating the synthesis gas stream and the steam cracker off gas stream into a hydrogen product stream comprising hydrogen from the synthesis gas stream and hydrogen from the steam cracker off gas stream, a carbon dioxide product stream comprising carbon dioxide, and a second off gas stream comprising methane from the steam cracker off gas stream and methane from the synthesis gas stream and carbon monoxide from the synthesis gas stream, wherein the hydrogen separation unit comprises a pressure swing adsorption unit, a membrane separation unit, or combinations thereof, or wherein the carbon dioxide separation unit comprises a cryogenic fractionation unit, a solvent based unit, or combinations thereof, or both;

passing the hydrogen product stream to the steam cracking zone as fuel gas;

passing the second off gas stream from the common separation zone to the hydrogen production zone;

recovering the carbon dioxide product stream;

expanding the hydrogen product stream to form a chilled hydrogen product stream;

recovering power from the expander;

chilling at least one stream in the common separation zone with the chilled hydrogen stream forming a warm hydrogen stream; and recovering the warm hydrogen stream wherein separating the synthesis gas stream and the steam cracker off gas stream further comprises:

separating the synthesis gas stream in the hydrogen separation unit to form a hydrogen product stream enriched in hydrogen and a hydrogen-depleted tail gas stream;

separating the hydrogen-depleted stream in the carbon dioxide separation unit to form the carbon dioxide-enriched product stream and an overhead stream;

separating the overhead stream in a second PSA unit to form a low-pressure carbon dioxide stream enriched in carbon dioxide and a third off-gas stream enriched in hydrogen and carbon monoxide or methane or both;

mixing the steam cracker off gas stream with the third off-gas stream to form a fourth off-gas stream;

introducing the fourth off-gas stream to the hydrogen production zone.

17. The process of claim 16 wherein separating the synthesis gas stream and the steam cracker off gas stream comprises:

compressing the hydrogen-depleted tail gas stream in a tail gas compressor to form a compressed tail gas stream;

drying the compressed tail gas stream to form a dried compressed tail gas stream; and recycling the low-pressure carbon dioxide stream to the tail gas compressor;

wherein separating the hydrogen-depleted tail gas stream in the carbon dioxide separation unit comprises separating the dried compressed tail gas stream.

18. The process of claim 17 wherein introducing the fourth off-gas stream to the hydrogen production zone comprises:

separating the fourth off-gas stream in a first membrane separation unit forming a first permeate stream comprising hydrogen and a first retentate stream comprising the carbon monoxide or the methane or both; and introducing the first retentate stream into the hydrogen production unit.

19. The process of claim 18 further comprising:

separating the first retentate stream in a second membrane separation unit into a second retentate stream comprising the carbon monoxide or the methane or both and a second permeate stream comprising hydrogen;

compressing the second permeate stream in a second compressor forming a compressed second permeate stream; and introducing the compressed second permeate stream into the first membrane separation unit;

or compressing the steam cracker off gas stream in the second compressor forming a compressed steam cracker off gas stream; and introducing the compressed steam cracker off gas stream into the first membrane separation unit;

or both.

20. The process of claim 17 wherein introducing the fourth off-gas stream to the hydrogen production zone comprises:

separating the fourth off-gas stream in a third PSA unit into a second hydrogen product stream and a second tail gas stream comprising carbon monoxide or methane or both;

compressing the second tail gas stream in a second tail gas compressor forming a second compressed tail gas stream;

separating the second compressed tail gas stream in a membrane separation unit into a first retentate stream comprising the carbon monoxide or the methane or both and a first permeate stream comprising hydrogen;

compressing the first permeate stream in a permeate compressor forming a compressed first permeate stream;

introducing the compressed first permeate stream into the third PSA unit.

* * * * *